United States Patent
Cinbis

(10) Patent No.: US 7,734,345 B2
(45) Date of Patent: Jun. 8, 2010

(54) METHOD AND SYSTEM FOR ABORTING CARDIAC TREATMENTS

(75) Inventor: Can Cinbis, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 563 days.

(21) Appl. No.: 11/391,949

(22) Filed: Mar. 29, 2006

(65) Prior Publication Data

US 2007/0239214 A1     Oct. 11, 2007

(51) Int. Cl.
*A61N 1/00* (2006.01)
(52) U.S. Cl. .......................................................... 607/5
(58) Field of Classification Search .................... 607/5, 607/6, 46
See application file for complete search history.

(56) References Cited

U.S. PATENT DOCUMENTS

| | | | |
|---|---|---|---|
| 5,662,689 A * | 9/1997 | Elsberry et al. ................. 607/5 |
| 5,792,205 A | 8/1998 | Alt et al. | |
| 5,817,131 A | 10/1998 | Elsberry et al. | |
| 5,987,356 A | 11/1999 | DeGroot | |
| 6,068,651 A | 5/2000 | Brandell | |
| 6,298,267 B1 * | 10/2001 | Rosborough et al. ........... 607/6 |
| 6,804,554 B2 * | 10/2004 | Ujhelyi et al. .................. 607/6 |
| 6,934,582 B2 * | 8/2005 | Thong et al. .................... 607/5 |
| 7,047,071 B2 * | 5/2006 | Wagner et al. .................. 607/4 |
| 2002/0120300 A1 | 8/2002 | Thong et al. | |

OTHER PUBLICATIONS

International Search Report, PCT/US2007/063808, Aug. 22, 2007, 6 Pages.

* cited by examiner

*Primary Examiner*—George Manuel
*Assistant Examiner*—Shubatra Narayanaswamy
(74) *Attorney, Agent, or Firm*—Michael C. Soldner

(57) ABSTRACT

One method for aborting cardiac treatments includes detecting an arrhythmia in a heart of a patient with at least one electrode, which is located outside the heart of the patient. An alarm signal is generated after the detection of the arrhythmia to alert a user of an impending cardiac treatment. The cardiac treatment is cancelled if an abort signal is provided by the user within a predetermined amount of time.

17 Claims, 4 Drawing Sheets

METHOD AND SYSTEM FOR ABORTING CARDIAC TREATMENTS

TECHNICAL FIELD

The present invention generally relates to cardiac treatment methods and systems, and more particularly relates to methods and systems for aborting cardiac treatments for cardiac arrhythmias.

BACKGROUND

In recent years, the use of implantable medical devices, such as pacemakers and defibrillators, has become increasingly common. Such devices are now used not only to detect, treat, and terminate cardiac arrhythmias, such as atrial tachycardia (AT), ventricle tachycardia (VT), atrial fibrillation (AF), and ventricle fibrillation (VF), but to prevent them altogether using specific pacing methods.

One type of device is commonly known as a subcutaneous implantable cardioverter defibrillator (ICD). Unlike a conventional (i.e., transvenous) ICD, the electrodes of a subcutaneous ICD are not deployed within the heart of the patient. Rather, the electrodes are simply implanted under the skin, near the heart. The subcutaneous ICD senses a patient's heart rhythm and classifies it according to a number or rate zones to detect episodes of tachycardia and/or fibrillation. The ICD then treats the arrhythmia with electric shocks delivered from the electrodes.

One difficulty associated with subcutaneous ICDs is that because the electrodes are not located within the heart, the accuracy with which arrhythmias are detected can be compromised. As a result, the subcutaneous ICD may falsely detect arrhythmias and provide unnecessary treatments. Additionally, even if the arrhythmia is properly detected, the patient may not want to have the treatment delivered for various reasons.

Accordingly, there is a need to provide a method and system for aborting cardiac treatments which may be delivered in response to a detected arrhythmia. Furthermore, other features and characteristics of the present invention will become apparent from the subsequent detailed description and the appended claims, taken in conjunction with the accompanying drawings and the foregoing technical field and background.

BRIEF SUMMARY

A method is provided for aborting cardiac treatments with a subcutaneous ICD. An arrhythmia in a heart of a patient is detected with at least one electrode, which is located outside the heart of the patient. An alarm signal is generated after said detection of the arrhythmia to alert a user of an impending cardiac treatment. The cardiac treatment is cancelled if an abort signal is provided by the user within a predetermined amount of time.

A system is provided for aborting cardiac treatments with a subcutaneous ICD. The system includes a housing, a lead connected to the housing, first and second electrodes respectively connected to the housing and the lead, an alarm signal generator, a user interface device, and a processor within the housing and electrically connected to the first and second electrodes, the alarm signal generator, and the user interface device. The processor is configured to detect an arrhythmia in a heart of a patient with at least one of the first and second electrodes, generate an alarm signal with the alarm signal generator after said detection of the arrhythmia to alert the patient of an impending cardiac treatment, cancel the cardiac treatment if an abort signal is received from the user interface device within a predetermined amount of time, and deliver the cardiac treatment with at least one of the first and second electrodes if the abort signal is not received from the user interface device within the predetermined amount of time.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description. It should also be understood that FIGS. 1-4 are merely illustrative and may not be drawn to scale.

Figure 1:
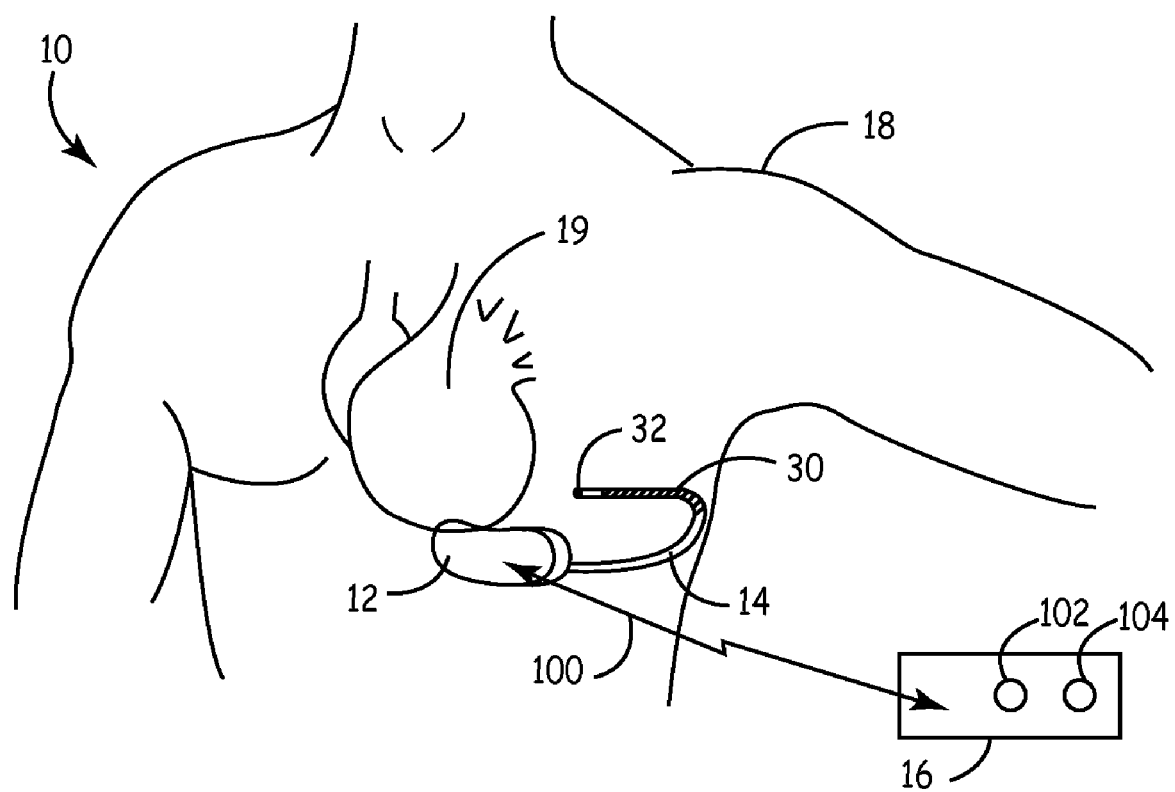
FIG. 1 is an isometric view of a cardiac treatment system, including an implantable cardiac device and a lead illustrated in FIG. 1.
Figure 2:
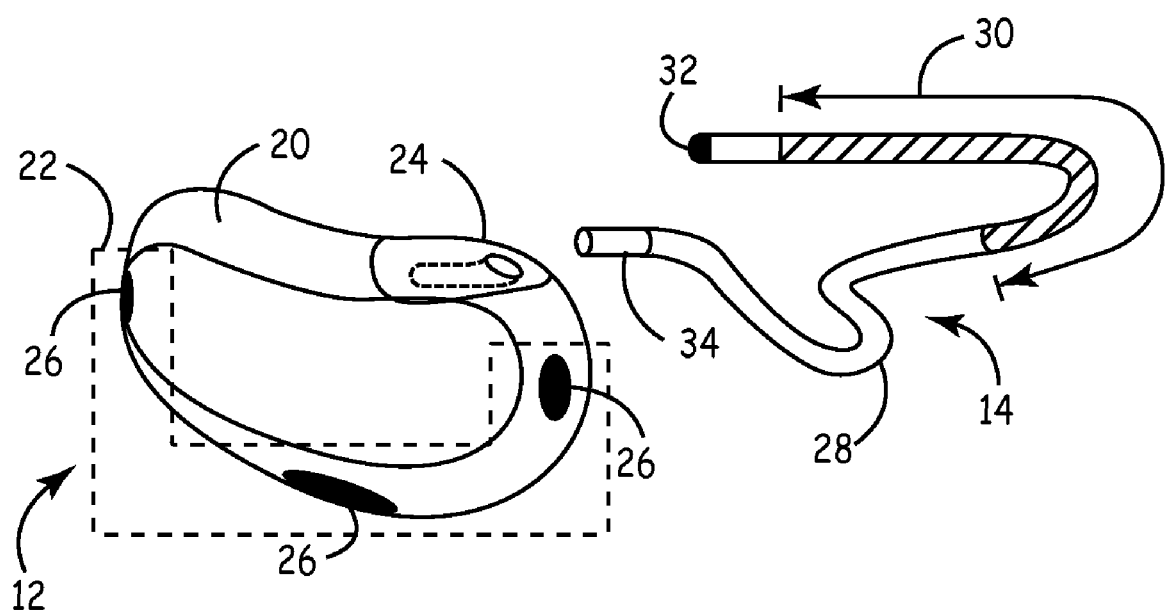
FIG. 2 is an isometric view of the implantable cardiac device and the lead.

FIGS. 1 and 2 illustrate a cardiac treatment system 10 according to one embodiment of the present invention. The system 10 includes a subcutaneous implantable cardioverter defibrillator ("ICD") 12, a subcutaneous sensing and cardioversion/defibrillation (CV/DF) therapy delivery lead 14, and an external controller 16. As shown in FIG. 1, the ICD 12 has been surgically implanted into a patient 18. For example, the ICD 12 may be implanted outside of the ribcage of the patient 18, anterior to the cardiac notch and near the heart 19 of the patient 18.

As illustrated in FIG. 2, the ICD 12 includes a housing 20, a subcutaneous electrode array (SEA) 22, and a connector 24. In the embodiment illustrated, the housing 20 is substantially ovoid with a kidney-shaped profile and may be constructed of, for example, steel, titanium, and/or a ceramic material. As will be discussed in greater detail below, the housing 20 includes electronic circuitry hermetically sealed and enclosed therein. The electronic circuitry enclosed within the housing 20 of the ICD 12 may be incorporated on a polyimide flex circuit, printed circuit board (PCB), or ceramic substrate with integrated circuits packaged in leadless chip carriers and/or chip scale packaging (CSP). As will be appreciated by one skilled in the art, the shape of the housing facilitates the implantation process and minimizes patient discomfort during normal body movement and flexing of the thoracic musculature.

The SEA 22 includes three electrodes 26, each of which is welded to the housing 20 at a flattened portion thereof and electrically connected to the electronic circuitry within the housing 20 of the ICD 12. The electrodes 26 may be constructed of, for example, flat plates or spiral electrodes. In the embodiment illustrated in FIG. 2, the electrodes 26 are arranged to form orthogonal signal vectors, as is commonly understood. The connector 24 is attached to the housing 20 and shaped to connect the subcutaneous lead 14 to the electronics circuitry within the housing 20.

The subcutaneous lead 14 includes an insulated flexible lead body 28, a distal defibrillation coil electrode 30, a distal sensing electrode 32, and a proximal connector pin 34. Referring to FIGS. 1 and 2 in combination, the proximal connector pin 34 is inserted into the connector 24 and the lead 14 is tunneled subcutaneously from the ICD 12 to a location adjacent to a portion of a latissimus dorsi muscle of the patient 18. In the embodiment illustrated, the lead 14 is tunneled subcutaneously from the ICD 12 laterally and posterially to the patient's back such that the ICD 12 and the distal coil electrode 30 lie on substantially opposing sides of the heart 19 of the patient 18.

Figure 3:
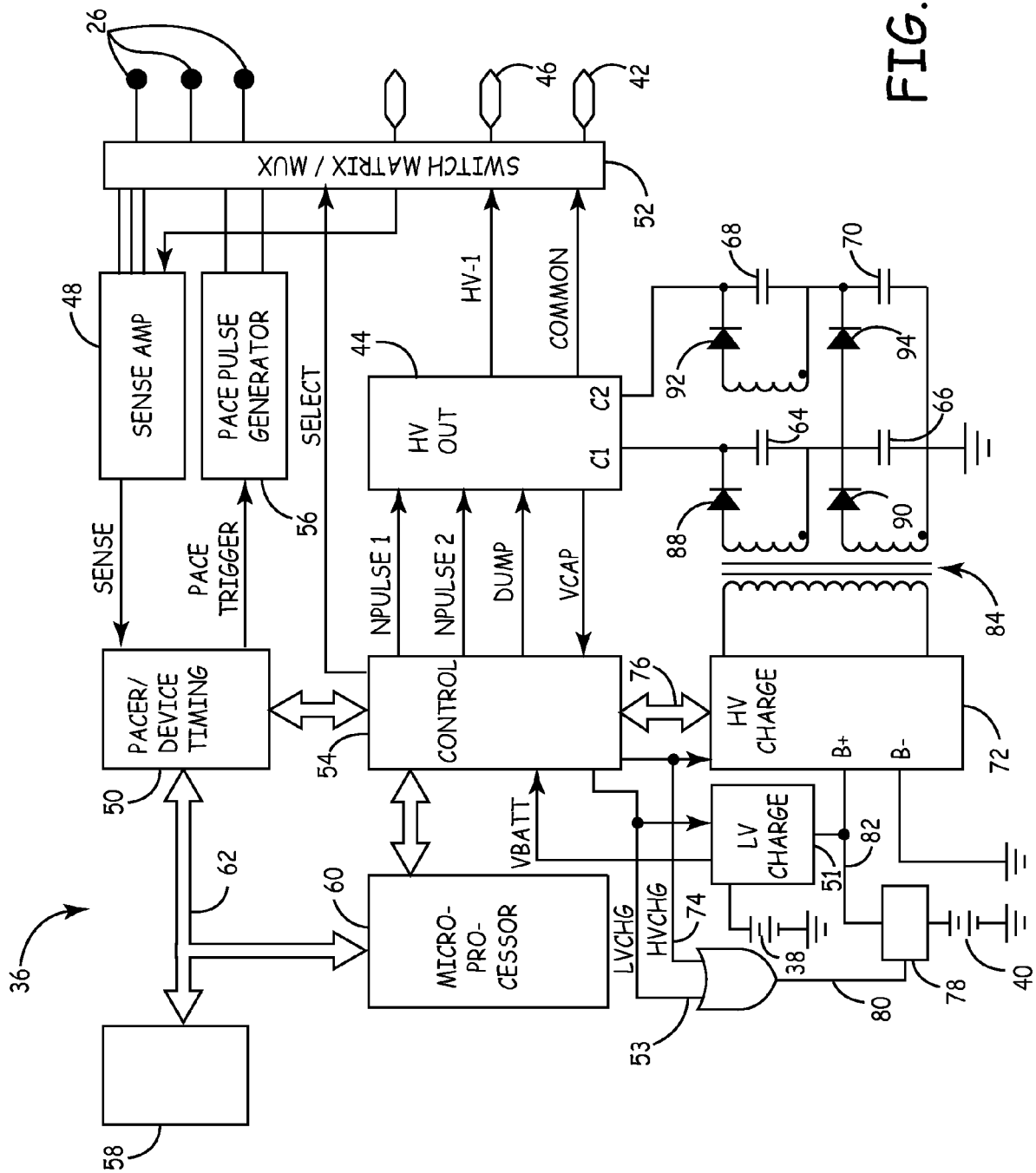
FIG. 3 is a block diagram of a system within the implantable cardiac device illustrated in FIG. 1.

FIG. 3 illustrates the electronic circuitry 36 (or ICD processor) within the housing 20 of the ICD 12 according to one embodiment of the present invention. The electronic circuitry 36 employed in ICD 12 may take any form that detects an arrhythmia from a sensed electrocardiogram (ECG), and/or electrogram (EGM), signal and provides CV/DF treatment or therapy, such as electrical shocks. Pacing therapy capabilities may also be provided including anti-tachycardia pacing (ATP) therapies, such as Atrial Preference Pacing (APP), burst pacing, ramp pacing, and ramp-plus pacing, and post-shock pacing sometimes needed while the heart recovers from a CV/DF shock. It will be understood that the simplified block diagram does not show all of the conventional components and circuitry that may be included in ICDs including digital clocks and clock lines, low voltage power supply and supply lines for powering the circuits and providing pacing pulses, or telemetry circuits for telemetry transmissions between the ICD 12 and the external controller 16.

As shown in FIG. 3, a low voltage battery 38 and a high voltage battery 40 are coupled to power supplies (or a single power supply) that supply power to the ICD circuitry 36. The low voltage battery 38 may include, for example, one or two conventional lithium carbon monofluoride ($LiCF_x$), lithium manganese dioxide ($LiMnO_2$), or lithium iodine ($LiI_2$) cells. The high voltage battery 40 may include, for example, one or two conventional lithium silver vanadium oxide (LiSVO) or $LiMnO_2$ cells.

The ICD functions are controlled by means of software, firmware and hardware that cooperatively monitor the ECG signals, determine when a CV/DF shock or ATP is necessary, and deliver prescribed CV/DF shock and ATP therapies according to programmed tiered-therapy menus. A CV/DF shock is delivered using an SEA electrode 26, as shown in FIG. 2, coupled to a COMMON output 42 of a high voltage output circuit 44 and the CV/DF electrode 30 disposed posterially and subcutaneously and coupled to a HV-1 output 46 of the high voltage output circuit 44.

Still referring to FIG. 3, a sense amplifier 48 in conjunction with a pacer/device timing circuit 50 processes the ECG sense signal that is received across a particular ECG sense vector defined by a selected pair of the SEA electrodes 26. The selection of the sensing electrode pair is made through a switch matrix/MUX 52 in a manner to provide the most reliable sensing of the ECG signal of interest. The ECG signals (e.g., far field ECG signals) are passed through the switch matrix/MUX 52 to the input of the sense amplifier 48, which, in conjunction with the pacer/device timing circuit 50, evaluates the sensed ECG signal. Bradycardia, or asystole, is typically determined by the expiration of an escape interval timer within the pacer timing circuit 50 and/or a control circuit 54 which is power with a low voltage charge circuit 51 through LVCHG line 53. Pace trigger signals are applied to a pacing pulse generator 56 to trigger pacing pulse generation upon expiration of an escape interval timer. Bradycardia pacing is often temporarily provided to maintain cardiac output after delivery of a CV/DF shock that may cause the heart to slowly beat as it recovers back to normal function.

The detection of a malignant tachycardia is determined in the control circuit 54 as a function of the intervals between R-wave sense event signals that are output from the pacer/device timing 50 and sense amplifier circuit 48 to the timing and the control circuit 54. Interval based signal analysis as well as ECG morphology analysis and processing of other sensor signals may be incorporated in arrhythmia detection schemes used by the ICD 12.

A sensor 58, such as a hemodynamic sensor or an oxygen sensor, as well as sensors to detect tissue color, tissue oxygenation, respiration, patient activity and the like may be used to detect a physiological condition of the patient 18 and contribute to the decision to apply or withhold a defibrillation therapy. An oxygen sensor may be located in the ICD pocket or, alternatively, located on the lead 14 to enable sensing of contacting or near-contacting tissue oxygenation or color. A hemodynamic sensor or heart rate sensor may be used in the detection of syncope. A predetermined threshold for each type of physiological condition may be stored within the circuitry 36, as will be described below.

Certain steps in the performance of arrhythmia detection algorithms are cooperatively performed in a microprocessor 60, including random access memory (RAM) and read-only memory (ROM), associated circuitry, and stored detection criteria that may be programmed into RAM via a telemetry interface. Data and commands are exchanged between the microprocessor 60 and the timing and control circuit 54, the pacer/device timing 50, and the high voltage output circuit 44 via a bi-directional data/control bus 62. The microprocessor 60 performs any necessary mathematical calculations, including tachycardia and fibrillation detection procedures, and updates time intervals monitored and controlled by the timers in the pacer/device timing circuitry 50 upon receiving an interrupt signal.

The arrhythmia detection algorithms used by the ICD 12 are highly sensitive and specific for the presence or absence of life threatening ventricular arrhythmias, such as ventricle tachycardia (VT) and ventricle fibrillation (VF), as well as atrial arrhythmias, such as atrial tachycardia (AT) and atrial fibrillation (AF).

As will be appreciated by one skilled in the art, event intervals (R-R intervals) are commonly used for detecting ventricular tachycardias. Additional information obtained from multiple cardiac signals, R-wave morphology, slew rate, other event intervals (P-R intervals) or other sensor signal information may be used in detecting, confirming or discriminating a tachycardia. In one detection scheme, programmable detection interval ranges designate the range of sensed event intervals indicative of a tachycardia and may be defined separately for detecting slow tachycardia, fast tachycardia and fibrillation. Sensed event intervals falling into defined detection interval ranges are counted to provide a count of tachycardia intervals. A programmable number of intervals to detect (NID) defines the number of tachycardia intervals occurring consecutively or out of a given number of preceding event intervals that are required to detect tachycardia. A separately programmed NID may be defined for detecting slow and fast tachycardia and fibrillation. In addition to the interval ranges and NID criteria, rapid onset criterion and rate stability criterion may also be defined for use in tachycardia detection schemes. Furthermore, a combined count of tachycardia and fibrillation intervals may be compared to a combined count threshold and, according to predefined criteria, used in detecting fibrillation or slow or fast tachycardia.

Still referring to FIG. 3, when a shock therapy is needed in response to an arrhythmia detection, high voltage capacitors 64, 66, 68, and 70 are charged to a pre-programmed voltage level by a high-voltage charging circuit 72. It is generally considered inefficient to maintain a constant charge on the high voltage output capacitors 64, 66, 68, and 70. Instead, charging may be initiated after an arrhythmia is detected. Specifically, the control circuit 54 issues a high voltage charge command HVCHG delivered on line 74 to a high voltage charge circuit 72, and charging is controlled by means of bi-directional control/data bus 76 and a feedback signal VCAP from the HV output circuit 44. The high voltage output capacitors 64, 66, 68 and 70 may be, for example, flat aluminum electrolytic or wet tantalum type capacitors.

A negative terminal of the high voltage battery 40 is directly coupled to system ground, and a positive terminal of the high voltage battery 40 is connected to a switch circuit 78. The switch circuit 78 is normally open so that the positive terminal of high voltage battery 40 is disconnected from the positive power input of the high voltage charge circuit 72. The high voltage charge command HVCHG is also conducted via conductor 80 to the control input of switch circuit 78, and switch circuit 78 closes in response to connect positive high voltage battery 40 voltage EXT B+ to the positive power input of high voltage charge circuit 72. The switch circuit 78 may be, for example, a field effect transistor (FET) with its source-to-drain path interrupting the EXT B+ conductor 82 and its gate receiving the HVCHG signal on conductor 74. The high voltage charge circuit 72 is thereby rendered ready to begin charging the high voltage output capacitors 64, 66, 68, and 70 with charging current from the high voltage battery 40.

The high voltage output capacitors 64, 66, 68, and 70 may be charged to very high voltages, e.g., 700-3150V, to be discharged through the body and heart of the patient between one of the SEA electrodes 26 and the CV/DF electrode 32 which are connected to the COMMON output 42 and a HV-1 output 46 of the high voltage output circuit 44, respectively. The voltages to which the capacitors 64, 66, 68, and 70 are charged may be associated with energies of about 25 Joules to about 210 Joules. The total high voltage capacitance could range from about 50 to about 300 microfarads. The high voltage capacitors 64, 66, 68, and 70 are charged by the high voltage charge circuit 72 and a high frequency, high-voltage transformer 84. Proper charging polarities are maintained by diodes 88, 90, 92, and 94 interconnecting the output windings of high-voltage transformer 84 and the capacitors 64, 66, 68, and 70. As noted above, the state of capacitor charge is monitored by circuitry within the high voltage output circuit 44 that provides a VCAP feedback signal indicative of the voltage to the control circuit 54. The control circuit 54 terminates the high voltage charge command HVCHG when the VCAP signal matches the programmed capacitor output voltage, i.e., the CV/DF peak shock voltage.

As will be described in greater detail below, the programmed shock therapy may be delayed for a predetermined amount of time (i.e., abort period). During the abort period, ATP therapies, such as those described above, may be delivered, contemporaneously with or prior to capacitor charging.

Upon termination of the abort period, control circuit 54 controls the delivery of the scheduled shock therapy. The control circuit 54 develops first and second control signals NPULSE 1 and NPULSE 2, respectively, that are applied to the high voltage output circuit 44 for triggering the delivery of cardioverting or defibrillating shocks. In particular, the NPULSE 1 signal triggers discharge of capacitors 64 and 66 (i.e., a first capacitor bank), and the NPULSE 2 signal triggers discharge of the first capacitor bank and a second capacitor bank, comprising capacitors 68 and 70. It is possible to select between a plurality of output pulse regimes simply by modifying the number and time order of assertion of the NPULSE 1 and NPULSE 2 signals. The NPULSE 1 signals and NPULSE 2 signals may be provided sequentially, simultaneously or individually. In this way, control circuitry 54 serves to control operation of the high voltage output stage 44, which delivers high energy CV/DF shocks between the pair of the CV/DF electrodes coupled to the HV-1 and COMMON outputs 46 and 42, as shown in FIG. 3.

The high HVCHG signal causes the high voltage battery 40 to be connected through the switch circuit 78 with the high voltage charge circuit 72 and the charging of output capacitors 64, 66, 68, and 70 to commence. Charging continues until the programmed charge voltage is reflected by the VCAP signal, at which point control and timing circuit 54 sets the HVCHG signal low terminating charging and opening switch circuit 78. Typically, the charging cycle takes only five to twenty seconds, and occurs very infrequently. The ICD 12 can be programmed to attempt to deliver cardioversion shocks to the heart in timed synchrony with a detected R-wave or without attempting to synchronize the delivery to a detected R-wave. Episode data related to the detection of the tachyarrhythmia and delivery of the CV/DF shock can be stored in RAM for uplink telemetry transmission to an external programmer as is well known in the art to facilitate in diagnosis of the patient's cardiac state.

Referring again to FIG. 1, the external controller 16 is in operable communication with the ICD 12, in particular the circuitry 36 illustrated in FIG. 3, through a communications link 100. The communications link 22 may be, for example, an electrical wire or a radio frequency link, such as Bluetooth, wireless fidelity (WiFi), or Medical Implant Communications System (MICS), as is commonly understood in the art. The external controller 16 includes an alarm signal generator 102 and a user input device 104. The alarm signal generator 102 may be any device suitable for alerting a user, such as the patient, of an impending cardiac treatment. Examples include a speaker to create an audible alarm, a light bulb or light emitting diode (LED) to create a visible alarm, and/or an actuator to vibrate. The user input device 104 may be, for example, a button which may be pressed by the user and/or a sensor capable of detecting particular types of responses from the user (e.g., voice commands, tapping, shaking, etc.).

Figure 4:
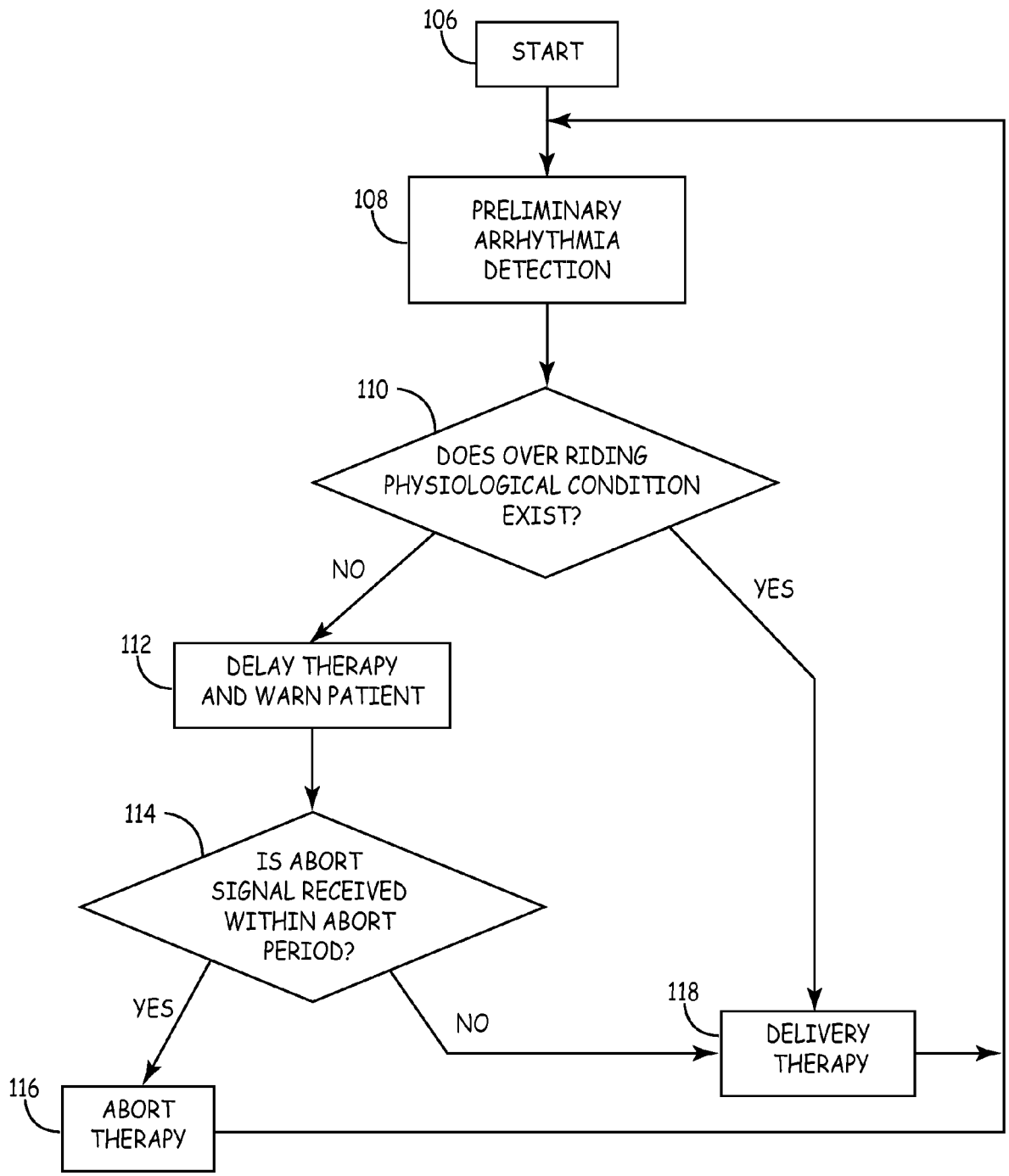
FIG. 4 is a flow chart of a method for providing a patient with an opportunity to override a cardiac treatment according to one embodiment of the present invention.

FIG. 4 illustrates a method for providing a patient an opportunity to abort a cardiac treatment, which may be implemented with the ICD 12 and the electronic circuitry 36 described above, according to one embodiment of the present invention. As will be appreciated by one skilled in the art, FIG. 4 is intended to illustrate the functional operation of the device, and should not be construed as reflective of a specific form of software or hardware necessary to practice an embodiment of the present invention. The particular form of software or hardware will be determined primarily by the particular system architecture employed in the device and by the particular detection and therapy delivery methodologies employed by the device. Providing software to accomplish the present invention in the context of any modern ICD, given the disclosure herein, is within the abilities of one of skill in the art. At step 106, the method begins, generally with an ICD, which may be similar to that described above, being implanted in a patient as shown in FIG. 1.

At step 108, a preliminary arrhythmia detection is made based on sensed ECG/EGM signals and any other sensor signals in accordance with a programmed tachycardia detection scheme, as described above. The arrhythmia may be, for example, VT, VF, AT, or AF.

It is then determined, at step 110, whether or not an overriding physiological condition exists which calls for a cardiac therapy (e.g., an electric shock) to be immediately delivered. Such overriding physiological conditions may relate to blood pressure, blood oxygen saturation, respiration, or any other condition that the device is capable of monitoring. The physiological condition may be detected via the sensor 58, as shown in FIG. 3. As will be appreciated by one skilled in the art, such an overriding physiological condition may indicate that the patient's health may be at serious risk unless the therapy is delivered immediately. The determination of whether or not a particular physiological condition is "overriding" may be based on the detected state of the condition compared to the predetermined threshold set for that condition.

If an overriding physiological condition does not exist, the process continues to step 112. At step 112, the cardiac therapy is delayed for a predetermined amount of time (i.e., abort period) while the alarm signal generator 102 on the external controller creates an alarm signal to alert the patient, or another user, that an arrhythmia has been detected and a cardiac treatment is imminent. As described above, the signal may be visible, audible, and/or tactile, depending on the type of alarm signal generator 102. The abort period may be between, for example, 10 and 60 seconds. The length of the abort may depend on clinical outcomes, individual patient condition, and clinician preference.

Although not indicated in FIG. 4, capacitor charging may also be initiated at some point between step 108 and step 112 such that the capacitors (64, 66, 68, and 70 in FIG. 3) are fully charged, or nearly fully charged, by the end of the abort period. It should be understood that capacitor charging may be initiated later in the abort delay period or even at the end of the abort period as long as the total shock delay time and capacitor charging time does not unacceptably delay the delivery of a shock.

At step 114, it is determined whether or not an abort signal was received from the user input device 104 on the external controller 16. After receiving the alarm, the patient can abort the impending cardiac treatment by activating the user interface device 104 within the abort period to send the abort signal to the ICD 12. The method for sending such a signal may be determined by the type of user interface device, as is described above. As will be appreciated by one skilled in the art, the patient 18 may wish to abort the cardiac treatment for such reasons as the patient 18 has just experienced an event which the patient 18 knows may cause the ICD 12 to falsely detect a tachycardia or the patient 18 feels healthy and believes that a treatment is not necessary. If the ICD 12 receives an abort signal within the abort period, at step 116, the cardiac treatment is aborted, and the process returns to step 108 for the detection of the next arrhythmia.

As shown at step 118, if an abort signal is not received within the abort period, it is assumed that the patient 18 either has received the alarm signal, believes that the cardiac treatment is necessary, and has appropriately prepared (e.g., by pulling off the road if operating an automobile), or is unable to respond. In either case, an appropriate cardiac treatment, such as a CV/DF shock, is delivered to the heart, as described above.

Thus, referring again to FIG. 1, the ICD 12 monitors the patient's 18 heart 19 for arrhythmias, and upon detection of an arrhythmia, warns the patient 18 that an electrical shock is about to be delivered to the heart 19 of the patient 18. The delivery of the electrical shock is delayed for a predetermined amount time, and if within that time an abort signal is received from a user interface device that is accessible to the patient, the delivery of the electrical shock is aborted. In this way, the patient 18 is given an opportunity to cancel the treatment if he or she wishes to do so.

One advantage of the method and system described above is that the patient (or another user) can abort the impending cardiac treatment if the patient wishes to do so. As a result, the number of unnecessary, and possibly hazardous, cardiac treatments are decreased.

Other embodiments may not have the alarm signal generator and/or the user interface device on an external controller. For example, as indicated above, the alarm signal generator may take the form of an actuator to create a vibration and the user interface device may take the form of a sensor to detect a tactile response, such as tapping. In such an embodiment, the actuator and the sensor may be located on (or within) the housing of the ICD such that the patient feels a vibration at the location of the ICD to warn of an impending cardiac treatment. Likewise, the patient may abort the treatment by tapping the ICD (i.e., tapping near where the ICD is implanted).

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A method for providing treatment for a cardiac arrhythmia comprising:
   detecting an arrhythmia in a heart of a patient with at least one electrode, the at least one electrode not coupled to the heart of the patient;
   detecting a physiological condition of the patient;
   generating an alarm signal after said detection of the arrhythmia to alert a user of an impending cardiac treatment;
   canceling the cardiac treatment if an abort signal is provided by the user within a predetermined amount of time;
   delivering the cardiac treatment before the predetermined amount of time if the physiological condition of the patient exceeds a predetermined threshold; and
   delivering the cardiac treatment if an abort signal is not provided by the user within the predetermined amount of time, the treatment delivered via first and second delivering electrodes, wherein the first and second delivering electrodes are configured to be positioned on substantially opposing front and rear sides of the heart of a patient without any electrode being directly connected thereto.

2. The method of claim 1, further comprising delivering the cardiac treatment to the heart after the predetermined amount of time if the abort signal is not received within the predetermined amount of time.

3. The method of claim 2, wherein the cardiac treatment is delivered with the at least one electrode.

4. The method of claim 3, wherein the at least one electrode is located subcutaneously within the patient.

5. The method of claim 4, wherein the at least one electrode includes first and second electrodes positioned on respective first and second substantially opposing sides of the heart of the patient.

6. The method of claim 5, wherein the first electrode is on an implantable cardioverter defibrillator (ICD) implanted subcutaneously in the patient on the first side of the heart and the second electrode is on a delivery lead connected to the ICD.

7. The method of claim 1, wherein said delivery of the cardiac treatment includes applying a voltage across the first and second electrodes to deliver an electrical shock to the heart of the patient.

8. The method of claim 7, wherein the voltage is stored in at least one capacitor within the ICD and further comprising charging the at least one capacitor before the predetermined amount of time.

9. The method of claim 8, wherein the user is the patient and the patient provides the abort signal via a user interface device in operable communication with the ICD.

10. A method for providing treatment for a cardiac arrhythmia comprising:
   detecting an arrhythmia in a heart of a patient with an implantable cardioverter defibrillator (ICD) implanted subcutaneously within the patient, the ICD being electrically connected to first and second electrodes positioned outside the heart of the patient;
   detecting a physiological condition of the patient;
   generating an alarm signal with an alarm signal generator in operable communication with the ICD after said detection of the arrhythmia to alert the patient of an impending cardiac treatment;
   canceling the cardiac treatment if an abort signal is received from a user interface device in operable communication with the ICD within a predetermined amount of time;
   delivering the cardiac treatment before the predetermined amount of time if the physiological condition of the patient exceeds a predetermined threshold;
   delivering the cardiac treatment with the first and second electrodes if the abort signal is not received within the predetermined amount of time; and
   charging the at least one capacitor after said detection of the arrhythmia and within the predetermined amount of time;
   wherein the first and second electrodes are configured to be positioned on substantially opposing front and rear sides of the heart of a patient and without being coupled thereto.

11. The method of claim 10, wherein said delivery of the cardiac treatment includes applying a voltage across the first and second electrodes to deliver an electrical shock to the heart and the voltage is stored in at least one capacitor within the ICD.

12. The method of claim 11, wherein the first electrode is on the ICD and the second electrode is on a lead connected to the ICD and the first and second electrodes are positioned on respective first and second substantially opposing sides of the heart of the patient.

13. The method of claim 12, wherein the predetermined amount of time is between approximately 10 and 60 seconds.

14. An implantable cardioverter defibrillator (ICD) system comprising:
   a housing;
   a lead connected to the housing;
   first and second electrodes respectively connected to the housing and the lead, wherein the first and second electrodes are configured to be positioned on substantially opposing front and rear sides of the heart of a patient without being directly connected thereto;
   an alarm signal generator;
   a user interface device; and
   a processor within the housing and electrically connected to the first and second electrodes, the alarm signal generator, and the user interface device, the processor configured to:
      detect an arrhythmia in a heart of a patient with at least one of the first and second electrodes;
      generate an alarm signal with the alarm signal generator after said detection of the arrhythmia to alert the patient of an impending cardiac treatment;
      cancel the cardiac treatment if an abort signal is received from the user interface device within a predetermined amount of time; and
      deliver the cardiac treatment with at least one of the first and second electrodes if the abort signal is not received from the user interface device within the predetermined amount of time; and
   a sensor not connected to the heart and in operable communication with the processor to detect a physiological condition in the heart and wherein the processor is further configured to deliver the cardiac treatment before the predetermined amount of time if the physiological condition of the patient exceeds a predetermined threshold.

15. The system of claim 14, further comprising a power supply and at least one capacitor within the housing and wherein said delivery of the cardiac treatment includes applying a voltage across the first and second electrodes to deliver an electrical shock to the heart of the patient, the voltage is stored in the at least one capacitor, and the processor is further configured to begin charging the at least one capacitor after said detection of the arrhythmia and within the predetermined amount of time.

16. The system of claim 15, further comprising an external controller in operable communication with the processor, at least one of the alarm signal generator and the user interface device being on the external controller.

17. The system of claim 15, wherein at least one of the alarm signal generator and the user interface device are connected to the housing.

* * * * *